United States Patent [19]
Gallagher et al.

[11] Patent Number: 5,484,935
[45] Date of Patent: Jan. 16, 1996

[54] PHARMACEUTICAL COMPOUNDS

[75] Inventors: Peter T. Gallagher, Yateley; Terence A. Hicks, Fleet; William M. Owton, Lightwater, all of England

[73] Assignee: Lilly Industries Limited, Basingstoke, England

[21] Appl. No.: 289,045

[22] Filed: Aug. 11, 1994

[30] Foreign Application Priority Data

Aug. 13, 1993 [GB] United Kingdom .............. 9316912

[51] Int. Cl.$^6$ .............. C07D 257/04; C07C 69/017; A61K 31/22; A61K 31/18
[52] U.S. Cl. .............. 548/253; 548/251; 562/466; 562/473; 564/84; 560/142; 560/100; 560/138
[58] Field of Search .............. 548/253, 251; 514/381, 534, 569, 602, 548; 562/466, 473; 564/80; 560/138, 100, 142

[56] References Cited

U.S. PATENT DOCUMENTS

| | | | |
|---|---|---|---|
| 3,873,538 | 3/1975 | Oxford et al. | 260/247.2 |
| 3,984,429 | 10/1976 | Peel et al. | 260/308 |
| 3,984,534 | 10/1976 | Peel et al. | 424/45 |
| 3,987,088 | 10/1976 | Hodson et al. | 260/475 |
| 4,244,968 | 1/1981 | Friedmann | 424/308 |

FOREIGN PATENT DOCUMENTS

| | | |
|---|---|---|
| 0243968 | 11/1987 | European Pat. Off. . |
| 0570091 | 11/1993 | European Pat. Off. . |
| WO92/10464 | 6/1992 | WIPO . |

OTHER PUBLICATIONS

Alexander et al., "Methylation and Hydroxylation Studies on Aloe-emodin," *J. Org. Chem.*, 45, 20–24 (1980).
Beilsteins Handbuch der Organischen Chemie, (4th ed., 3d Supp.), vol. 10, Part 5, 4787–4790, 1972.

*Primary Examiner*—David B. Springer
*Attorney, Agent, or Firm*—James P. Leeds

[57] ABSTRACT

Pharmaceutical compounds of the formula

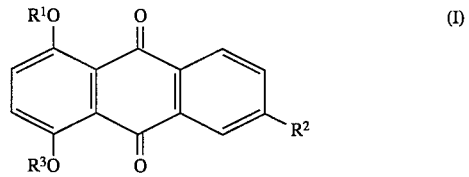

in which $R^1$ and $R^3$ are each $C_{1-4}$ alkyl or $C_{1-4}$ alkylcarbonyl, and $R^2$ is carboxy, tetrazolyl, $C_{1-4}$ alkyl-sulphonamido or —$CR^4R^5CO_2H$ where $R^4$ and $R^5$ are each hydrogen or $C_{1-4}$ alkyl; provided that when $R^1$ and $R^3$ are both methyl and when $R^1$ and $R^3$ are both methylcarbonyl, $R^2$ is not carboxy; and salts and esters thereof.

5 Claims, No Drawings

PHARMACEUTICAL COMPOUNDS

This invention relates to pharmaceutical compounds and their preparation.

There are many anthraquinone (9,10-dihydro-9,10-dioxoanthracene) compounds disclosed in the literature and they are described as having a variety of uses. British Patent 1 578 452 discloses some compounds of this type which are related to the well-known compound rhein.

The present invention relates to pharmaceutical compounds of the formula:

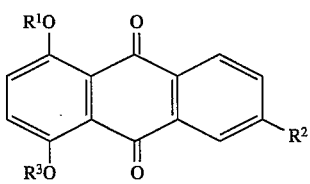

in which $R^1$ and $R^3$ are each $C_{1-4}$ alkyl or $C_{1-4}$ alkyl-carbonyl, and $R^2$ is carboxy, tetrazolyl, $C_{1-4}$ alkyl-sulphonamido or $-CR^4R^5CO_2H$ where $R^4$ and $R^5$ are each hydrogen or $C_{1-4}$ alkyl; provided that when $R^1$ and $R^3$ are both methyl and when $R^1$ and $R^3$ are both methylcarbonyl, $R^2$ is not carboxy; and salts and esters thereof.

The compounds of the invention are indicated for use in the treatment of connective tissue matrix diseases such as osteoarthritis, and in the treatment of cancer.

A preferred group of compounds is one in which $R^1$ and $R^3$ are each $C_{1-4}$ alkyl or $C_{1-4}$ alkyl-carbonyl, and $R^2$ is carboxy, tetrazolyl, $C_{1-4}$ alkyl-sulphonamido or $-CR^4R^5CO_2H$ where $R^4$ and $R^5$ are each hydrogen or $C_{1-4}$ alkyl; provided that when $R^1$ and $R^3$ are both $C_{1-4}$ alkylcarbonyl, $R^2$ is not carboxy; and salts and esters thereof.

A $C_{1-4}$ alkyl group can be branched or unbranched, and includes methyl, ethyl, propyl, isopropyl and butyl, and is preferably methyl. The groups $R^4$ and $R^5$ are preferably each hydrogen or methyl.

Preferred compounds are those in which $R^1$ and $R^3$ take the same value.

Specific examples of compounds according to the invention are as follows:
5-(9,10-dihydro-5,8-dimethoxy-9,10-dioxo-anthracen-2-yl)tetrazole,
5-(5,8-diacetoxy-9,10-dihydro-9,10-dioxoanthracen-2-yl)tetrazole,
N-(9,10-dihydro-5,8-dimethoxy-9,10-dioxoanthracen-2-yl)methanesulphonamide,
N-(5,8-diacetoxy-9,10-dihydro-9,10-dioxoanthracen-2-yl)methanesulphonamide,
9,10-dihydro-5,8-dimethoxy-9,10-dioxoanthracen-2-yl acetic acid,
5,8-diacetoxy-9,10-dihydro-9,10-dioxoanthracen-2-yl acetic acid;
or salts thereof.

The compounds of the invention can exist in salt form derived from any of the well known bases. Preferably such salts are pharmaceutically-acceptable, but other salts are included as they may serve as intermediates in the purification of compounds or in the preparation of other salts, or are useful for identification, characterisation or purification. Examples are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

The compounds can also be utilised in ester form, esters being formed at the 2-carboxy group. These can be any of the well known ester groups, both aliphatic and aromatic. Preferred esters are those derived from an alcohol or an aminoalcohol, and particularly preferred are alkyl esters such as an ester of a $C_{1-4}$ alcohol, especially the methyl or ethyl ester.

The invention also includes a process for producing a compound of formula (I), above, which comprises:

1) hydrolysing a compound of the formula:

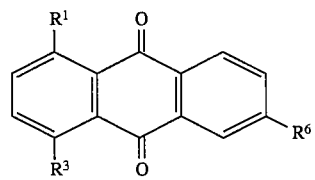

in which $R^6$ is $-CN$ or $-CR^4R^5CN$, to give a compound of formula (I) in which $R^2$ is, respectively, carboxyl or $-CR^4R^5CO_2H$, 2) converting a compound of the formula (II) in which $R^6$ is $-CN$ to a compound of formula (I) in which $R^2$ is tetrazolyl, 3) reacting a compound of the formula:

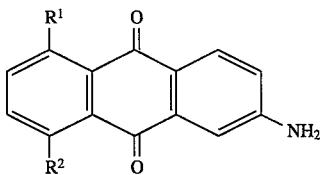

with a reactant of the formula $R^4SO_2X$, where X is halo, to give a compound of the formula (I) in which $R^2$ is $C_{1-4}$ alkylsulphonamido; or 4) reacting a compound of the formula:

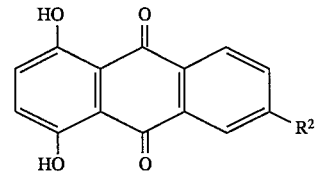

with a $C_{1-4}$ alkylating agent or an acylating agent.

With regard to process variant (1), the reaction is preferably carried out in an aqueous medium employing, for example, an acid or base, at a temperature of from 20° C. to 100° C.

Compounds of formula (II) used in the above reaction are either known or can be produced by well known preparative methods. For example, compounds in which $R^6$ is $-CN$ can be prepared from the corresponding compound of formula:

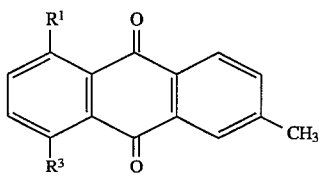

by standard procedures of bromination, conversion to the aldehyde and aldoxime derivative, and from these to the nitrile. Compounds of formula (V) can be synthesised by condensation of 1,4-dihydroxybenzene with 4-methyl phthalic alhydride, and subsequent modification of the 9,10-dihydro-5,8-dihydroxy-9,10-dioxo-2-methylanthracene. Compounds of formula (II) in which $R^6$ is —$CR^4R^5CN$ can be prepared from compounds of the formula:

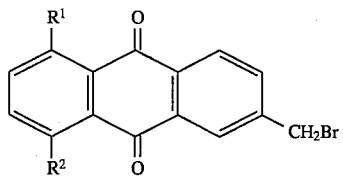

produced by bromination of compounds of formula (V) followed by reaction with cyanide, and optional alkylation in the case of compounds in which $R^4$ or $R^5$ is $C_{1-4}$ alkyl.

With regard to process variant (2), the tetrazole derivative can be prepared by reacting the nitrile with metal azide, for example sodium azide, preferably in an organic solvent such as, for example, dimethylformamide, and at a temperature of from 0° C. to 200° C.

With regard to process variant (3), the reaction is preferably carried out in an organic solvent at a temperature of, for example, from −50° C. to 100° C. The sulphonylating agent is preferably of the formula $R^4SO_2Cl$.

Compounds of formula (III) can be prepared from the corresponding 2-nitro compound prepared by condensation according to the method for compound (V) above. The nitro derivative can be reduced to the compound of formula (III) employing for example titanium trichloride in aqueous dimethyl formamide. Alternatively, the compound of formula (III) can be prepared from a compound of formula (I) in which $R^2$ is carboxy via the carbonyl azide and isocyanate.

It will be appreciated that the alkoxy and acyloxy derivatives of formula (I) can be derived from the corresponding 5,8-dihydroxy compound of formula (IV), by conventional means. The reaction preferably employs dimethylsulphate or an alkyl halide, especially the bromide, or acylating acid or anhydride such as, for example, glacial acetic acid or acetic anhydride.

As mentioned above, the compounds are indicated for use in the treatment of osteoarthritis and allied connective tissue diseases such as, for example, osteoporosis and rheumatoid arthritis. Such diseases are often characterised by an increase in matrix synthesis and remodelling. Incorporation of newly synthesised components into a biological and biomechanically functional matrix is, however, frequently deficient. Drugs which modulate the activity of the cells involved in such connective tissue matrix maintenance and repair are, therefore, of potential use in such diseases.

The compounds produce dose-dependent inhibition of in vitro tumour cell proliferation with IC50 values ranging from 1–50 μM. Partial inhibitory effects of around 30% were also observed for several compounds on tumour cell protein synthesis at a concentration of 100 μM using a method similar to that described by A. Floridi et al, Exp. Mol. Pathol., 1985, 42, 293–305. The majority of the compounds also inhibited mitogen-induced lymphocyte proliferation with IC50 values ranging from 10–100 μM.

Further modulatory effects of the compounds were observed in an in vitro model system used to study the differentiation of chondrocytes from prechondrogenic stem cells, as described by D. F. Paulsen et al, In Vitro Cellular and Developmental Biology 24, 138–147. The compounds demonstrate bimodal concentration effects on the production of matrix components by differentiating chick limb bud chondrocytes. Inhibitory effects of up to 95% were observed at concentrations ranging from 10–100 μM, whereas at submicromolar concentrations the compounds produced up to a three-fold stimulation in the synthesis of matrix macromolecules.

Further evidence of activity has been provided by studying the effect of compounds of the invention on lesions in guinea pigs. Spontaneous lesions of osteoarthritis were first described in the hind knee joints of old guinea pigs by Silverstein and Sokoloff (Arthritis Rheum. 1, 82–86 (1958)). Bendele and Hulman (Arthritis Rheum. 31, 561–565 (1988)) and Bendele, White and Hulman (Lab. Anim. Sci. 39, 115–121 (1989)) studied younger animals and were the first to describe the time course of progressing osteoarthritis in outbred male guinea pigs. These latter studies were confirmed and extended by Meacock, Bodmer and Billingham (J. Exp. Path. 71, 279–293 (1990)), also in outbred male guinea pigs.

The compounds of the invention are thus indicated for use in the treatment of osteoarthritis and allied connective tissue matrix diseases such as, for example, osteoporosis and rheumatoid arthritis. Furthermore, the inhibitory properties on tumour cell proliferation indicate that the compounds are of potential in the treatment of cancer.

The invention also includes a pharmaceutical composition comprising a pharmaceutically acceptable diluent or carrier in association with one or more of the above compounds or a pharmaceutically acceptable salt thereof.

The compounds may be administered by various routes, for example by the oral or rectal route, topically or parenterally, for example by injection or infusion, being usually employed in the form of a pharmaceutical composition. Such compositions are prepared in a manner well known in the pharmaceutical art and comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, ointments containing, for example, up to 10% by weight of the compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydrobenzoate, talc magnesium stearate and mineral oil. The compositions of the injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the conditions to be treated, the choice of compound to be administered and the chosen route of administration, and therefore the above dosage ranges are not intended to limit the scope of the invention in any way.

The invention is illustrated by the following Examples.

EXAMPLE 1

1. 9,10-Dihydro-5,8-dihydroxy-9,10-dioxoanthracene-2-carboxylic acid

Anhydrous aluminium chloride (75 g) and freshly dried (at ~310° C.) sodium chloride (15 g) were heated in a oil-bath, with mechanical stirring, to give a melt. The temperature of the melt was increased to 160° C., when addition of a finely ground intimate mixture of 1,2,4-benzene tricarboxylic anhydride (10.8 g) and hydroquinone (4.425 g), in a portionwise manner, was begun. Addition took 43 minutes, during which time the temperature had risen to 170° C. The now deep crimson-coloured reaction mixture was stirred for a further 1 hour at 165°–170° C. The bulk of the molten mass was poured into ice/water (500 ml). The aqueous solution was then used to wash out the reaction flask.

Concentrated HCl (50 ml) was added and the mixture heated on a steam bath for ~16 minutes. The resulting rust-coloured suspension was cooled in an ice-bath for 10 minutes, then filtered. The reddish-brown solid on the filter was washed with water (3×500 ml), then dried at 60° C. in vacuo. (2.5 g) of the product was soxhlet extracted with dioxan (250 ml) for 20 hours, stirred at room temperature for 5 hours and filtered to remove the reddish-brown solid which was washed on the filter with 40°–60° C. petrol (total 200 ml) and dried at 70° C. in vacuo.

2. 9,10-Dihydro-5,8-dimethoxy-9,10-dioxoanthracene-2-carboxylic acid, methyl ester A mixture of 9,10-dihydro-5,8-dihydroxy-9,10-dioxoanthracene-2-carboxylic acid (23 g), anhydrous potassium carbonate (166 g) and dimethyl sulphate (63.9 g) in acetone (2.5 L) and dioxan (2 L) was mechanically stirred and heated under reflux for 44.3 hours.

The reaction mixture was then filtered hot and the contents of the filter were washed with hot dioxan (4×250 ml). The combined filtrate and washings were evaporated at 62° C. in vacuo to remove the bulk of the solvents.

The residue was diluted with 40°–60° C. petroleum ether (1.25 L). The resulting suspension was filtered to remove the rust coloured solid product. After washing with 40°–60° C. petrol (0.5 L), then drying at 72° C. in vacuo, the required product was obtained, m.p. 214°–216° C.

3. 9,10-Dihydro-5,8-dimethoxy-9,10-dioxoanthracene-2-carboxylic acid 9,10-Dihydro-5,8-dimethoxy-9,10-dioxoanthracene-2-carboxylic acid, methyl ester (0.8 g) and powdered potassium hydroxide (0.42 g) were magnetically stirred in water (4.3 ml), methanol (8.6 ml) and dimethyl sulphoxide (4.3 ml) for 22.25 hours at room temperature.

The resulting suspension was concentrated to remove the methanol, then water (16 ml) was added to effect dissolution.

0.5N hydrochloric acid was then added to adjust the solution to pH1.

The resulting reddish brown coloured precipitate was removed by filtration, then washed with water (150 ml).

After drying on a porous tile the solid had a melting point of 298°–299° C.

4. 9,10-Dihydro-5,8-dimethoxy-N-(1,1-dimethylethyl)-9,10-dioxanthracene-2-carboxamide 9,10-Dihydro-5,8-dimethoxy-9,10-dioxoanthracene-2-carboxylic acid (2.058 g), 1,2-dichloroethane (60 ml), dry pyridine (0.1 ml) and thionyl chloride (0.6 ml) were heated and stirred under reflux for 2.5 hours. Thionyl chloride (0.1 ml) was added and the mixture heated under reflux for 1 hour and cooled to room temperature. t-Butylamine (2.4 ml) was added during 3 minutes and stirred for 30 minutes, after which the reaction was complete and the mixture was filtered through a pad of Celite. The solvent was evaporated in vacuo to give the carboxamide as a solid, m.p. 158°–160° C.

5. 9,10-Dihydro-5,8-dimethoxy-9,10-dioxoanthracene-2-carbonitrile 9,10-Dihydro-5,8-dimethoxy-N-(1,1-dimethylethyl)-9,10-dioxoanthracene-2-carboxamide (2.086 g) in toluene (60 ml) was warmed to 95° C. with stirring. Phosphorus pentachloride (3.405 g) was added portionwise over 12 minutes at this temperature. The solution was then heated under reflux for 30 minutes during which the colour lightened from black to orange. The heat was removed and the mixture allowed to cool, naturally producing orange crystals. These were removed by filtration, washed with toluene and water and dried in vacuo at 70° C. to give the carbonitrile as a solid, m.p. 220°–222.5° C.

6. 5-(9,10-Dihydro-5,8-dimethoxy-9,10-dioxoanthracene-2-yl)-1H-tetrazole 9,10-Dihydro-5,8-dimethoxy-9,10-dioxoanthracene-2-carbonitrile (1.005 g), sodium azide (0.334 g), triethylamine hydrochloride (0.708 g), dimethyl formamide (24 ml) and water (0.5 ml) were heated with stirring to 97° C. for 9 hours then cooled and poured into a mixture of water (210 ml) and 5N HCl (30 ml). The precipitate formed was isolated by filtration, washed with water and then dried in vacuo at 70° C. to give the tetrazole as a solid, m.p. 260°–262° C.

EXAMPLE 2

Soft Gelatin Capsule

Each soft gelatin capsule contains:

| Active ingredient | 150 mg |
| --- | --- |
| Arachis oil | 150 mg |

After mixing together, the blend is filled into soft gelatin capsules using the appropriate equipment.

EXAMPLE 3

Hard Gelatin Capsule

Each capsule contains:

| Active ingredient | 50 mg |
| --- | --- |
| PEG 4000 | 250 mg |

The PEG 4000 is melted and mixed with the active ingredient. Whilst still molten the mixture is filled into capsule shells and allowed to cool.

EXAMPLE 4

Tablets each containing 10 mg of active ingredient are made up as follows:

| Active ingredient | 10 mg |
| --- | --- |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

We claim:

1. A compound of the formula:

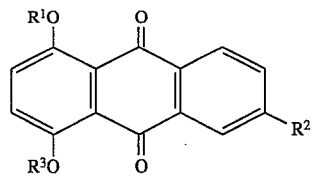

in which $R^1$ and $R^3$ are each $C_{1-4}$ alkyl or $C_{1-4}$ alkyl-carbonyl, and $R^2$ is carboxy, tetrazolyl, $C_{1-4}$ alkyl-sulphonamido or —$CR^4R^5CO_2H$ where $R^4$ and $R^5$ are each hydrogen or $C_{1-4}$ alkyl; provided that when $R^1$ and $R^3$ are both methyl and when $R^1$ and $R^3$ are both methylcarbonyl, $R^2$ is not carboxy; and pharmaceutically acceptable salts thereof.

2. A compound according to claim 1 in which $R^1$ and $R^3$ are each $C_{1-4}$ alkyl or $C_{1-4}$ alkyl-carbonyl, and $R^2$ is carboxy, tetrazolyl, $C_{1-4}$ alkyl-sulphonamido or —$CR^4R^5CO_2H$ where $R^4$ and $R^5$ are each hydrogen or $C_{1-4}$ alkyl; provided that when $R^1$ and $R^3$ are both $C_{1-4}$ alkyl and when $R^1$ and $R^3$ are both $C_{1-4}$-carbonyl, $R^2$ is not carboxy; and pharmaceutically-acceptable salts thereof.

3. A compound according to claim 1 which is 5-(9,10-dihydro-5,8-dimethoxy-9,10-dioxo-anthracen-2-yl)tetrazole, 5-(5,8-diacetoxy-9,10-dihydro-9,10-dioxoanthracen-2-yl)tetrazole, N-(9,10-dihydro-5,8-dimethoxy-9,10-dioxoanthracen-2-yl)methanesulphonamide, N-(5,8-diacetoxy-9,10-dihydro-9,10-dioxoanthracen-2-yl)methanesulphonamide, 9,10-dihydro-5,8-dimethoxy-9,10-dioxoanthracen-2-yl acetic acid, 5,8-diacetoxy-9,10-dihydro-9,10-dioxoanthracen-2-yl acetic acid;

or pharmaceutically-acceptable salts thereof.

4. A pharmaceutical formulation comprising a compound as defined in any of claims 1 to 3, or a pharmaceutically-acceptable salt thereof, together with a pharmaceutically-acceptable diluent or carrier therefor.

5. A method of treating an animal, including a human, suffering from or susceptible to a connective tissue matrix disease which comprises administering an effective amount of a compound as defined in claim 1, or a pharmaceutically acceptable salt thereof.

* * * * *